United States Patent [19]

Watson et al.

[11] 4,440,650

[45] Apr. 3, 1984

[54] PROCESS FOR ENHANCING RECOVERY OF OIL FROM OIL-BEARING EARTH FORMATIONS

[75] Inventors: James M. Watson; James R. Butler, both of Big Spring, Tex.

[73] Assignee: Cosden Technology, Inc., Dallas, Tex.

[21] Appl. No.: 317,213

[22] Filed: Nov. 2, 1981

[51] Int. Cl.$^3$ ................................................. C09K 3/00
[52] U.S. Cl. .............................. 252/8.55 D; 166/266; 166/275; 166/305 R; 260/686
[58] Field of Search ................... 252/8.55 D, 8.55 R; 166/274, 275, 265, 266, 305 R; 260/98, 686

[56] References Cited

U.S. PATENT DOCUMENTS

| | | | |
|---|---|---|---|
| 2,782,230 | 2/1957 | Seaton | 260/686 |
| 3,398,791 | 8/1968 | Hurd | 166/270 |
| 3,783,943 | 1/1974 | Schievelbein et al. | 166/266 |
| 3,913,673 | 10/1975 | Barber | 166/266 |
| 3,933,201 | 1/1976 | Kerfoot et al. | 252/8.55 D |
| 3,965,984 | 6/1976 | Clark et al. | 252/8.55 D |
| 4,082,146 | 4/1978 | Compton et al. | 166/266 |
| 4,121,663 | 10/1978 | Compton | 166/265 |
| 4,147,638 | 4/1979 | Plummer | 166/275 |
| 4,177,207 | 12/1979 | Nussbaum et al. | 252/8.55 D |
| 4,252,192 | 2/1981 | Nussbaum et al. | 166/275 |

FOREIGN PATENT DOCUMENTS

| | | | |
|---|---|---|---|
| 714354 | 7/1965 | Canada | 166/274 |
| WO79/00007-01 | 9/1979 | PCT Int'l Appl. | 252/8.514 |

OTHER PUBLICATIONS

Parkes, G., ed. 1952, Mellois Modern Inorganic Chemistry Longmans, Green and Co., New York, pp. 446–471.

*Primary Examiner*—Herbert B. Guynn
*Assistant Examiner*—Howard J. Locker
*Attorney, Agent, or Firm*—M. Norwood Cheairs

[57] ABSTRACT

A process for increasing recovery of oil from oil-bearing earth formations wherein $H_2S$ from sour wellhead gas is oxidized to $SO_3$ which in turn is reacted with a petroleum hydrocarbon mixture to produce a petroleum sulfonate. The petroleum sulfonate is incorporated into an oil recovery enhancing fluid and introduced through an injection well into an oil-bearing earth formation to displace oil toward a production well.

7 Claims, No Drawings

PROCESS FOR ENHANCING RECOVERY OF OIL FROM OIL-BEARING EARTH FORMATIONS

BACKGROUND OF THE INVENTION

This invention relates to a process for increasing the recovery of oil from oil-bearing earth formations. More particularly, the invention relates to a process for increasing oil recovery wherein an oil recovery enhancing fluid is introduced through an injection well into an oil-bearing earth formation and displaced through said formation toward a production well, and oil is recovered through said production well. Specifically, the present invention relates to a process for increasing oil recovery wherein the oil recovery enhancing fluid comprises surface active petroleum sulfonates.

Primary recovery techniques which rely upon natural forces to obtain oil from oil-bearing earth formations generally yield only a small proportion of the oil in the earth formation. It has been estimated that the oil obtained by primary recovery generally amounts to less than about 20% of the oil in place. Secondary recovery techniques, such as water flooding or steam injection, have been developed to increase the proportion of oil obtainable. While such techniques may result in increased recoveries, they typically still leave from 60 to 70% of the oil originally present in the formation. Further efforts by the art to improve oil recoveries have resulted in development of so-called tertiary recovery techniques. One promising tertiary technique involves introducing a slug of an oil recovery enhancing fluid comprising a surface active petroleum sulfonate through an injection well into an oil-bearing earth formation, displacing the slug through the formation toward a production well and recovering oil displaced from the earth formation by the fluid through the production well.

Although such methods may result in improved oil recoveries ranging up to 60% of the original oil in place, the usefulness of such methods is severely limited by their high cost. The expense of the surface active material used in forming the oil recovery enhancing fluid constitutes a large portion of the cost of such tertiary recovery methods.

Efforts to reduce the cost of such tertiary recovery techniques include attempts to produce the desired surface active materials in situ by injecting into the ground compounds which will react to form surface active substances. Examples of this approach are described in U.S. Pat. Nos. 3,392,782; 3,398,791; and 3,387,655. Unfortunately, the difficulties encountered in controlling the reactions involved render such methods less effective than desired.

It has also been proposed to sulfonate crude oil adjacent the well site to obtain surface active petroleum sulfonates which can be used to form oil recovery enhancing fluids; see U.S. Pat. No. 4,147,638. The procedure proposed in this patent relies on commercial sources of sulfonating agents and is still undesirably expensive.

SUMMARY OF THE INVENTION

Accordingly, it is the object of the present invention to provide an improved process for enhancing oil recovery from oil-bearing earth formations.

A further object of the present invention is to provide an improved process for producing surface active petroleum sulfonate materials.

Another object of the present invention is to provide a process for reducing the cost of oil recovery enhancing fluids.

It is also an object of the present invention to provide an improved process for producing petroleum sulfonates by processing crude oil adjacent the well site.

An additional object of the present invention is to provide an improved process for production of sulfur trioxide by oxidation of hydrogen sulfide.

Yet another object of the present invention is to provide an improved process for producing surface active materials suitable for use in oil recovery enhancing fluids wherein the surfactant material is produced substantially at the site where it is to be used.

A still further object of the present invention is to provide a new process for treating sour wellhead gas.

These and other objects of the invention are achieved by providing a process for enhancing oil recovery from oil-bearing earth formations comprising collecting sour wellhead gas from an existing well, oxidizing the hydrogen sulfide contained in the sour gas to sulfur trioxide at the well site, reacting the sulfur trioxide with a petroleum hydrocarbon mixture at the well site to produce a sulfonated petroleum mixture, adding a neutralizing agent to the sulfonated petroleum mixture to form a surface active petroleum sulfonate salt mixture, incorporating the petroleum sulfonate salt mixture into an oil recovery enhancing fluid, and injecting the oil recovery enhancing fluid into an oil-bearing earth formation.

In preferred aspects of the invention, the hydrogen sulfide from the wellhead gas is concentrated by extracting it with a suitable solvent such as an organic amine; the oxidation of the hydrogen sulfide is carried out by a two-stage procedure involving initial oxidation of hydrogen sulfide to sulfur dioxide followed by catalytic oxidation of the sulfur dioxide to sulfur trioxide; water is separated from the sulfur dioxide prior to the catalytic oxidation; unsulfonated hydrocarbons are separated from sulfonated hydrocarbons after the sulfonation reaction; and the oil recovery enhancing fluid is an oil and water microemulsion or micellular emulsion.

DETAILED DESCRIPTION OF PREFERRED EMBODIMENTS

In addition to liquid petroleum, oil wells commonly yield gases, termed wellhead gases. Neglecting air contamination, the principal components of wellhead gases are light hydrocarbons containing from one to five carbon atoms. In many cases, wellhead gases are sour gases. That is to say, they contain appreciable amounts of acidic sulfur compounds, principally hydrogen sulfide. Depending upon the specific oil field, the hydrogen sulfide content of sour wellhead gases may range from about 1 to about 15 mole percent.

Typically, hydrocarbon-containing wellhead gases are collected and used as fuel gases. In the case of sour gases, they may be transported to a gas sweetening plant for removal of hydrogen sulfide from the bulk of the hydrocarbon material, prior to use.

According to the present invention, sour wellhead gases containing hydrogen sulfide are collected at the wellhead, and the hydrogen sulfide is oxidized with atmospheric air to produce sulfur dioxide and water.

Preferably, for use in the process of the present invention, the $H_2S$ content of the wellhead gas will be at least about 2 mole percent. If desired, the hydrogen sulfide can be extracted from the wellhead gas prior to the combustion operation. For this purpose, organic amines or other suitable solvents may be used. Suitable solvents include diisopropyl amine, diglycol amine, diethyl amine, and similar materials.

The hydrogen sulfide stream is routed to a reaction furnace along with a controlled amount of oxygen and oxidized to $SO_2$. The temperature of the furnace is maintained from about 650° to about 700° C. (1200°–1300° F.).

The oxidized gas stream containing sulfur dioxide and water is then cooled to condense the water vapor and introduced into a separator where the water is separated from the sulfur dioxide containing gases. If further drying of the gas stream is desired, conventional drying agents such as silica gel or anhydrous calcium chloride may be used.

The resulting sulfur dioxide-containing gas stream is admixed with a controlled amount of oxygen, heated to a suitable temperature and catalytically oxidized to sulfur trioxide. Preferred catalysts for use in the catalytic oxidation step include vanadium pentoxide and/or spongy platinum black. Suitable reaction temperatures range between 300° and 800° C., preferably 400° to 600° C. Oxidation to sulfur trioxide is more highly favored at lower temperatures. Accordingly, the catalytic reaction may be carried out in several stages with cooling of the reaction gas stream between stages. Further control of the reaction may be obtained by appropriately regulating the amount of oxygen introduced to each of the catalytic reaction stages. It has also been found desirable to use a sulfur dioxide feed stream which is not highly concentrated. Preferably, the feed stream will contain between about 5 and about 15 mole percent sulfur dioxide.

Further details of suitable catalytic oxidation processes are disclosed in Mandelik et al, "Selective Oxidation in Sulfuric . . . Acid Plants . . . " *Process Technology and Flowsheets;* pages 93–97; V. Cavaseno, ed.; McGraw Hill (1979), which is hereby incorporated herein by reference.

Sulfur trioxide recovered from the final catalytic oxidation stage is used to prepare surface active hydrocarbon sulfonates at the well site. If desired, the sulfur trioxide may be purified by conventional techniques, or the raw sulfur trioxide may be used as is.

Hydrocarbons to be used in producing the desired surface active sulfonates include crude oil and crude oil fractions. It is particularly preferred to use crude oil in the process of the invention because it is readily available at the well site by merely diverting to the sulfonation apparatus a portion of the oil recovered from a nearby producing well. Sulfonation is preferably effected in the liquid phase using an agitated reactor, a tubular back mix reactor or a film type reactor. Generally between 5 and 30 parts by weight sulfur trioxide are introduced into the reaction zone for every 100 parts hydrocarbon. Particularly advantageous results are obtained when the hydrocarbon contains a substantial aromatic proportion, e.g. greater than or equal to 25 mole percent aromatics. Reaction temperatures may range between about 25° C. (80° F.) and about 120° C. (250° F.), preferably between about 55° C. (130° F.) and about 80° C. (180° F.). The reaction may be carried out at ambient pressure, or elevated pressures may be maintained in the reactor. If desired, substantially inert solvents such as chlorinated hydrocarbons may be included in the reaction mixture to facilitate handling.

Further details of suitable sulfonation processes are disclosed in U.S. Pat. Nos. 3,924,681; 3,938,591; 3,964,548; 4,147,638 and/or 4,177,207; the disclosures of which are hereby incorporated herein by reference.

The sulfonated reaction mixture is then neutralized with a neutralizing agent to produce a surface active petroleum sulfonate salt. Particularly preferred neutralizing agents include aqueous alkali metal hydroxides and/or ammonia. Generally a slight excess of neutralizing agent is used to assure complete neutralization of all of the sulfonate groups.

The neutralized mixture is thereafter permitted to separate into a supernatant phase comprising primarily unsulfonated hydrocarbons and a lower phase containing substantially all of the surface active petroleum sulfonates. The unsulfonated hydrocarbons are then separated, e.g. by decantation, and the surface active petroleum sulfonates are used to form an oil recovery enhancing fluid.

Suitable oil recovery enhancing fluids vary from dilute aqueous surfactant solutions to complicated oil and water microemulsions. Details of producing suitable oil recovery enhancing fluids are well-known in the art as described in the patent and technical literature (see H. K. Van Poolen and Associates, *Fundamentals of Enhanced Oil Recovery,* Chapter 4, Pennwell Publishing (1980) and Shah and Schecter, *Improved Oil Recovery by Surfactant and Polymer Flooding,* Academic Press (1977).

A slug of the oil recovery enhancing fluid is introduced into an oil-bearing earth formation through an injection well and displaced through the formation toward a production well. The surfactant-containing fluid releases and drives oil from the formation toward the production well where it is recovered.

Further details of the invention will become apparent from a consideration of the following non-limiting example:

EXAMPLE

Sour well head gas comprising approximately 10 mole percent hydrogen sulfide and the balance light hydrocarbons is collected from an operating well and conveyed to an extraction unit adjacent the well site where the hydrogen sulfide is extracted from the balance of the gas with diisopropyl amine. The hydrogen sulfide is distilled from the amine, mixed with a stoichiometric amount of air and introduced into an oxidation furnace maintained at a temperature of approximately 675° C. In the furnace, the hydrogen sulfide is substantially quantitatively oxidized to sulfur dioxide and water. The product gas stream withdrawn from the reaction furnace is cooled to approximately 30° C. to condense the water, and the condensate is separated from the remaining gases. The dried sulfur dioxide containing gas stream is thereafter diluted with substantially inert gases, e.g. carbon dioxide and nitrogen to a sulfur dioxide concentration of approximately 8 mole percent, and introduced in stages through the beds of a three-bed catalytic reactor system containing a commercially available vandium pentoxide oxidation catalyst. Between stages, the partially oxidized gas stream is cooled to a temperature between 400° and 450° C. before being introduced into the next catalytic reactor stage. Oxygen additions and contact times within the reactor are controlled to prevent the outlet temperature of the gas stream exiting from each bed from exceeding 700° C. The sulfur trioxide containing gases recovered from the catalytic oxidation are then routed to a film type reactor where they contact a film of crude petroleum comprising an aromatic fraction of 25 mole percent. The sulfonated oil is neutralized with aqueous sodium hydroxide, and allowed to stand until it separates into two phases. The supernatant hydrocarbons are decanted and the remaining surface active petroleum sulfonate is used to form an oil and water microemulsion suitable for use as an oil recovery enhancing fluid.

The foregoing embodiments have been described merely as illustrative examples of the invention and are not intended to be limiting. Since modifications of the disclosed embodiments incorporating the spirit and substance of the invention may occur to persons skilled in the art, the scope of the invention is to be limited solely with respect to the appended claims and equivalents.

We claim:

1. A process for enhancing oil recovery from oil-bearing earth formations, comprising the steps of:
   (a) collecting $H_2S$-containing wellhead gas from an existing well;
   (b) concentrating the $H_2S$ from the wellhead gas, said concentrating step comprising extracting the $H_2S$ from the wellhead gas with an organic amine and thereafter distilling the $H_2S$ from the amine;
   (c) oxidizing the concentrated $H_2S$ to $SO_3$ at the well site;
   (d) reacting the $SO_3$ with crude petroleum at the well site to produce a sulfonated petroleum mixture, said crude petroleum being recovered from an operating well located in the same field as the well from which the $H_2S$-containing wellhead gas is recovered;
   (e) adding a neutralizing agent to the sulfonated mixture to form a surface active petroleum sulfonate salt mixture;
   (f) incorporating the petroleum sulfonate salt mixture into an oil recovery enhancing fluid; and
   (g) injecting the oil recovery enhancing fluid into an oil-bearing earth formation.

2. A process according to claim 1, wherein the oxidation of the $H_2S$ to $SO_3$ is effected by
   oxidizing $H_2S$ is in the presence of free molecular oxygen to produce a mixture of $H_2O$ and $SO_2$;
   condensing and separating $H_2O$ from the product mixture of the preceding step; and
   catalytically oxidizing $SO_2$ to $SO_3$ in the presence of free molecular oxygen and an oxidation catalyst selected from the group consisting of $V_2O_5$ and platinum metal catalysts.

3. A process according to claim 1 further comprising the step of separating unsulfonated hydrocarbons from said sulfonated hydrocarbon mixture.

4. A process according to claim 3, wherein said separation step is effected by
   allowing the sulfonated mixture to stand until it separates into a first phase comprising primarily unsulfonated hydrocarbon and a second phase comprising sulfonated hydrocarbon; and
   thereafter decanting the supernatant phase.

5. A process according to claim 1, wherein said neutralizing agent is selected from the group consisting of ammonia and alkali metal hydroxides.

6. A process according to claim 1, wherein said oil recovery enhancing fluid is an aqueous surfactant solution.

7. A process according to claim 1, wherein said oil recovery enhancing fluid is an oil and water emulsion.

* * * * *